United States Patent
Miyachi et al.

(10) Patent No.: US 6,730,687 B1
(45) Date of Patent: May 4, 2004

(54) SUBSTITUTED BENZYLTHIAZOLIDINE-2, 4-DIONE DERIVATIVES

(75) Inventors: Hiroyuki Miyachi, Kazo (JP); Masahiro Nomura, Nogi-machi (JP); Takahiro Tanase, Nogi-machi (JP); Koji Murakami, Oyama (JP); Masaki Tsunoda, Kasukabe (JP)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/049,645

(22) PCT Filed: Aug. 18, 2000

(86) PCT No.: PCT/JP00/05519
§ 371 (c)(1),
(2), (4) Date: Feb. 25, 2002

(87) PCT Pub. No.: WO01/14349
PCT Pub. Date: Mar. 1, 2001

(30) Foreign Application Priority Data

Aug. 23, 1999 (JP) .............................. 11-235527
Aug. 10, 2000 (JP) ......................... 2000-242706

(51) Int. Cl.[7] ..................... A61K 31/426; C07D 277/34
(52) U.S. Cl. ....................................... 514/369; 548/183
(58) Field of Search ........................... 548/183; 514/369

(56) References Cited

U.S. PATENT DOCUMENTS 5,223,522 A * 6/1993 Clark et al. ................. 514/369
5,753,681 A    5/1998 Fujiwara et al.

FOREIGN PATENT DOCUMENTS

| EP | 332331 | | 9/1989 |
| EP | 0 846 693 | * | 6/1998 |
| EP | 881219 | | 12/1998 |
| JP | 8-333355 | | 12/1996 |
| JP | 9-48771 | | 2/1997 |
| JP | 9-301963 | | 11/1997 |
| JP | 10-87640 | | 4/1998 |
| WO | 97/32863 | | 9/1997 |
| WO | WO 03/045945 A1 | | 6/2003 |

OTHER PUBLICATIONS

K. Murakami et al.: "A Novel Insulin Sensitizer Acts as a Coligand for Peroxisome Proliferator–Activated Receptor–a (PPAR–a) and PPAR–y" Diabetes, 47, pp. 1841–1847 1998.

M. Nomura et al.: "(3–Substituted Benzyl) thiazolidone–2, 4–diones as Structurally New Antihyperglycemic Agents-"Bioorg. Med. Chem. Lett., 9, pp. 533–538 02/99.

Ide Tomohiro et al.: "Zuker fatty Rat ni okeru Kanshishitsu Taisha taisuru PPAR a Kasseika no Eikyou" Diabetes Frontier, 9(3), pp. 345–346.

K. Murakami et al.: "Evidence for Direct Binding of Fatty Acids and Eicosanoids to Human Peroxisome Proliferators–Activated Receptor a" Biochem. Biophys., Res. Commun., 260, pp. 609–613 07/99.

* cited by examiner

Primary Examiner—Joseph K. McKane
Assistant Examiner—Rebecca Anderson
(74) Attorney, Agent, or Firm—Oblon, Spivak, McClelland, Maier & Neustadt, P.C.

(57) ABSTRACT

The invention provides novel substituted benzylthiazolidine-2,4-dione derivatives that bind to receptor to activate as ligands of human peroxisome proliferator-activated receptor (PPAR) and exhibit blood glucose-decreasing action and lipid-decreasing action, and processes for preparing them.

It relates to substituted benzylthiazolidine-2,4-dione derivatives represented by the general formula (1)

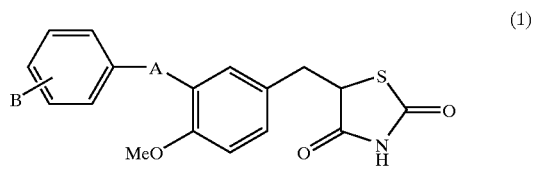

(1)

[wherein the bond mode of A denotes —CH$_2$CONH—, —NHCONH—, —CH$_2$CH$_2$CO— or —NHCOCH$_2$—, and B denotes a lower alkyl group with carbon atoms of 1 to 4, lower alkoxy group with carbon atoms of 1 to 3, halogen atom, trifluoromethyl group, trifluoromethoxy group, phenyl group which is unsubstituted or may have substituents, phenoxy group which is unsubstituted or may have substituents or benzyloxy group which is unsubstituted or may have substituents], their medicinally acceptable salts, their hydrates and processes for preparing them.

11 Claims, No Drawings

SUBSTITUTED BENZYLTHIAZOLIDINE-2, 4-DIONE DERIVATIVES

This application is a 371 of PCT/JP00/05519 filed Aug. 18, 2000.

TECHNICAL FIELD

The present invention relates to substituted benzylthiazolidine-2,4-dione derivatives effective for the prevention and/or therapy of metabolic diseases such as diabetes and hyperlipidemia as agonists of peroxisome proliferator-activated receptor (abbreviated as PPAR) being nuclear receptor, in particular, as agonists of human PPAR, their addition salts, processes for preparing them, and medicinal compositions containing these compounds.

BACKGROUND TECHNOLOGIES

The peroxisome proliferator-activated receptor(PPAR) is a ligand-dependent transcription factor that belongs to nuclear receptor superfamily similarly to steroid receptor, retinoid receptor, thyroid receptor, etc., and three isoforms ($\alpha$ type, $\beta$(or $\delta$) type and $\gamma$ type) with different histological distribution have been identified hitherto in human and various animal species (Proc. Natl. Acad. Sci., 1992, 89, 4653). Thereamong, the PPAR$\alpha$ is distributed in the liver, kidney, etc. with high catabolic capacity for fatty acids and, particularly high expression is recognized in the liver, (Endo-crinology, 1995, 137, 354), positively or negatively controlling the expressions of genes related to the metabolism and the intracellular transport of fatty acids (e.g. acyl CoA synthetic enzyme, fatty acid-binding protein and lipoprotein lipase) and apolipoprotein (AI, AII, CIII) genes related to the metabolisms of cholesterol and neutral lipid. The PPAR$\beta$ is expressed ubiquitously in the tissues or organisms, including nerve cells. At present, the physiological significance of PPAR$\beta$ is unclear. The PPAR$\gamma$ is highly expressed in the adipocytes and contributed to the differentiation of adipocytes (J. Lipid Res., 1996, 37, 907). In this way, each isoform of PPAR play specific functions in the particular organs and tissues.

Moreover, it is reported that a knock-out mouse of PPAR$\alpha$ exhibits hypertriglyceridemia with ageing and becomes obesity mainly by increasing the white adipose tissues (J. Biol. Chem., 1998, 273, 29577), hence the relevance between activation of PPAR$\alpha$ and decreasing action of lipids (cholesterol and triglyceride) in blood is suggested strongly.

On the other hand, fibrates and statins are widely used so far as the therapeutic drugs for hyperlipidemia. However, the fibrates have only weak decreasing action of cholesterol. while the statins have weak decreasing action of free fatty acids and triglycerides. Moreover, with respect to the fibrates, various adverse effects such as gastrointestinal injury, anthema, headache, hepatic disorder, renal disorder and biliary calculus are reported. The reason is considered to be due to that the fibrates exhibit extensive pharmacological function.

On the other hand, it is ascertained that the major intracellular target proteins of Troglitazone, Pioglitazone and Rosiglitazone, a series of thiazolidine-2,4-dione derivatives that are therapeutic drugs for type II diabetes (noninsulin-dependent diabetes) and exhibit blood sugar-decreasing action, improving action on hyperinsulinemia, etc. is PPAR$\gamma$, and these drugs increase the transactivation of PPAR$\gamma$ (Endocrinology, 1996, 137, 4189, Cell., 1995, 83, 803, Cell., 1995, 83, 813). Hence, PPAR$\gamma$-activator (agonist) that can augment the transactivation of PPAR$\gamma$ is important as antidiabetic drug.

As described, when considering the role of transcription factor called PPAR on the function on adipocytes and the controlling mechanisms of glucose metabolism and lipid metabolism, if a compound that binds directly to as a ligand of PPAR, in particular, human PPAR and can activate human PPAR could be created, it would be reasonable to expect the medicinal use as a compound that exhibits blood glucose-decreasing action and/or decreasing action of lipids (both of cholesterol and neutral lipid) in blood due to very specific mechanism.

For compounds having an affinity to PPAR$\alpha$ as ligands of PPAR$\alpha$, HETE (hydroxyeicosatetraenoic acid) produced via oxidation with cytochrome P-450 and eicosanoides in HEPE (hydroxyeicosapentaenoic acid) groups, in particular, 8-HETE, 8-HEPE, etc. are reported in addition to LTB., being a metabolite of arachidonic acid (Proc. Natl. Acad. Sci., 1997, 94, 312). However, these endogenous unsaturated fatty acid derivatives are unstable metabolically and chemically and cannot be offered as medicinal drugs.

Moreover, with Toroglitazone, the occurrence of serious adverse effect on liver is reported rarely, hence the development of a therapeutic drug for type II diabetes with effectiveness and high safety is being sought.

Now, as compounds with similar structure to the inventive substituted benzylthiazolidine-2,4-dione derivatives, thiazolidine-2,4-dione derivatives in Japanese Unexamined Patent Publication Nos. Sho 55-22636, Sho 60-51189, Sho 61-85372, Sho 61-286376, Hei 1-131169, Hei 2-83384, Hei 5-213913, Hei 8-333355, Hei 9-48771 and Hei 9-169746, European Patent Open No. 0441605, WO-92/07839, etc. are known. However, all of these compounds are thiazolidine-2,4-dione derivatives with different structure from the inventive compounds.

With regard to patents etc. reporting the agonistic effect on PPAR$\alpha$, WO-97/25042, WO-97/36579, etc. are reported, but all of these have different structure from the inventive compounds and the transactivation function of PPAR$\alpha$ is also never satisfied in strength.

Both the hyperlipidemia and the diabetes are risk factors of arterosclerosis and, from a viewpoint of the prevention of arterosclerosis, in particular, coronary arterosclerosis, the development of a therapeutic drug for metabolic diseases with effectiveness and high safety is desired clinically.

DISCLOSURE OF THE INVENTION

As a result of diligent studies paying an attention to such specific role on the lipid metabolism of human PPAR, aiming at the creation of structurally novel drug with effectiveness and high safety as a therapeutic drug for diabetes and a therapeutic drug for hyperlipidemia, the inventors have found that novel substituted benzylthiazolidine-2,4-dione derivatives represented by a following general formula (1) have excellent transactivation function on human PPAR, and exhibit the blood glucose-decreasing action and the lipid-decreasing action, leading to the completion of the invention.

Namely, the invention relates to substituted benzylthiazolidine-2,4-dione derivatives represented by a general formula (1)

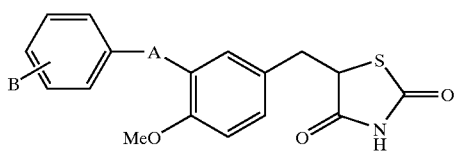
(1)

[wherein the bond mode of A denotes —CH$_2$CONH—, —NHCONH—, —CH$_2$CH$_2$CO— or —NHCOCH$_2$—, and B denotes a lower alkyl group with carbon atoms of 1 to 4, lower alkoxy group with carbon atoms of 1 to 3, halogen atom, trifluoromethyl group, trifluoro-methoxy group, phenyl group which is unsubstituted or may have substituents, phenoxy group which is unsubstituted or may have substituents or benzyloxy group which is unsubstituted or may have substituents], their medicinally acceptable salts and their hydrates.

The salts of the compounds represented by the general formula (1) in the invention are of common use and metal salts, for example, alkali metal salts (e.g. sodium salt, potassium salt, etc.), alkaline earth metal salts (e.g. calcium salt, magnesium salt, etc.), aluminum salt, and other pharmacologically acceptable salts are mentioned.

Moreover, the compounds represented by the general formula (1) in the invention sometimes include optical isomers based on thiazolidine-2,4-dione ring portion, but all of such isomers and their mixtures are to be included in the scope of the invention.

Furthermore, for the compounds represented by the general formula (1), the existence of various tautomers is considered. These are, for example, as shown in the following formulae.

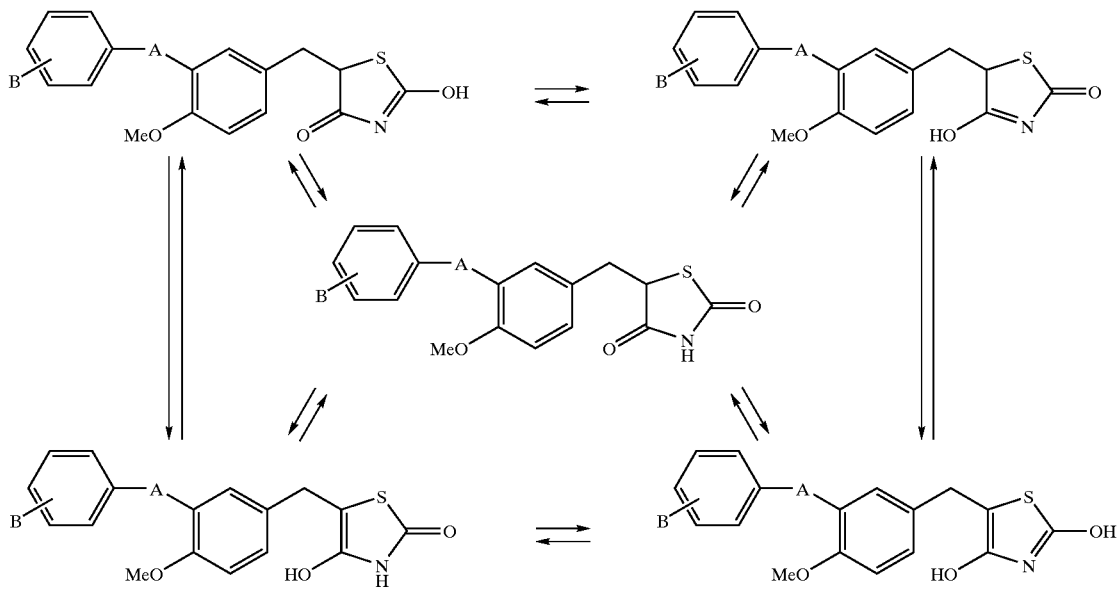

[wherein the bond mode of A denotes —CH$_2$CONH—, —NHCONH—, —CH$_2$CH$_2$CO— or —NHCOCH$_2$—, and B denotes a lower alkyl group with carbon atoms of 1 to 4, lower alkoxy group with carbon atoms of 1 to 3, halogen atom, trifluoromethyl group, trifluoromethoxy group, phenyl group which is unsubstituted or may have substituents, phenoxy group which is unsubstituted or may have substituents or benzyloxy group which is unsubstituted or may have substituents].

In the general formula (l) aforementioned, all of these isomers and their mixtures are to be included in the scope of this invention.

In the general formula (1) of the invention, for "lower alkyl group with carbon atoms of 1 to 4", straight chain or branched ones with carbon atoms of 1 to 4 such as methyl, ethyl, propyl, isopropyl and butyl are mentioned. For "lower malkoxy group with carbon atoms of 1 to 3", straight chain or branched ones with carbon atoms of 1 to 3 such as methoxy, ethoxy, isopropoxy and propoxy are mentioned.

For "halogen atoms", fluorine atom, chlorine atom, bromine atom and iodine atom are mentioned. For substituents acceptable in "phenyl group which is unsubstituted or may have substituents, phenoxy group which is unsubstituted or may have substituents or benzyloxy group which is unsubstituted or may have substituents", lower alkyl group with carbon atoms of 1 to 4, lower alkoxy group with carbon atoms of 1 to 3, and halogen atom are mentioned.

According to the invention, the compounds (1a), the bond mode of A portion being —NHCOCH$_2$— in the said general formula (1), can be prepared, for example, through following processes (Scheme 1).

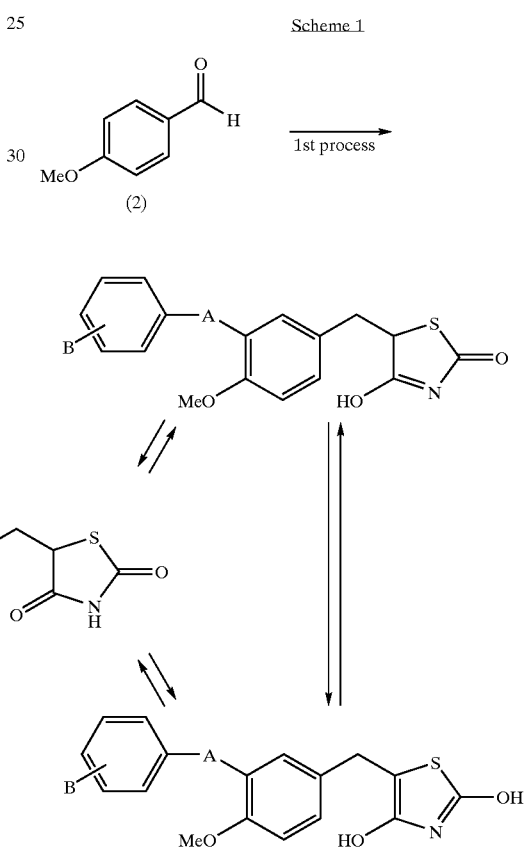

-continued

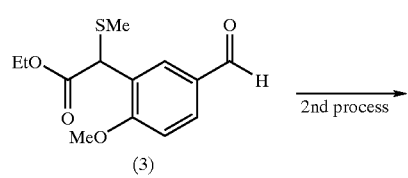

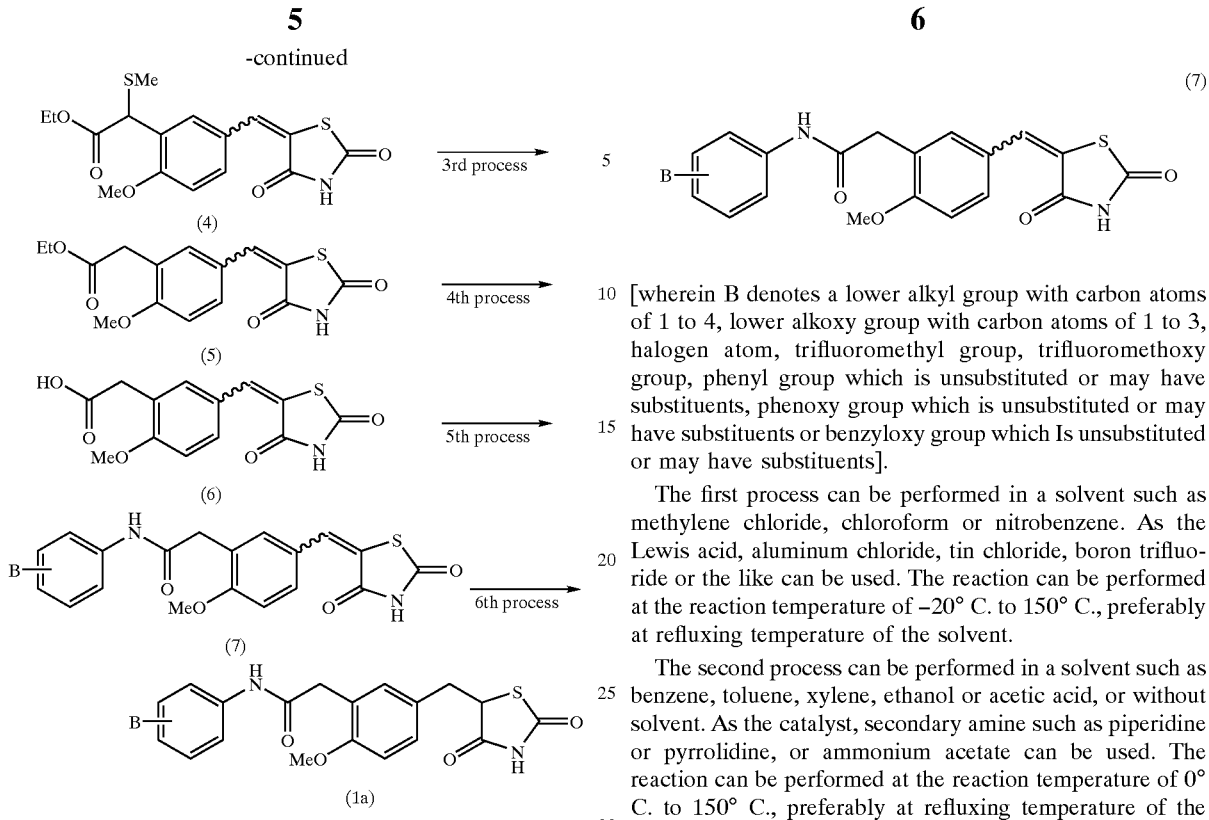

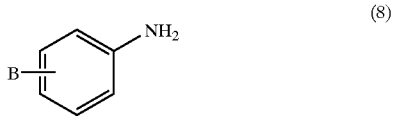

(7)

[wherein B denotes a lower alkyl group with carbon atoms of 1 to 4, lower alkoxy group with carbon atoms of 1 to 3, halogen atom, trifluoromethyl group, trifluoromethoxy group, phenyl group which is unsubstituted or may have substituents, phenoxy group which is unsubstituted or may have substituents or benzyloxy group which Is unsubstituted or may have substituents].

The first process can be performed in a solvent such as methylene chloride, chloroform or nitrobenzene. As the Lewis acid, aluminum chloride, tin chloride, boron trifluoride or the like can be used. The reaction can be performed at the reaction temperature of −20° C. to 150° C., preferably at refluxing temperature of the solvent.

The second process can be performed in a solvent such as benzene, toluene, xylene, ethanol or acetic acid, or without solvent. As the catalyst, secondary amine such as piperidine or pyrrolidine, or ammonium acetate can be used. The reaction can be performed at the reaction temperature of 0° C. to 150° C., preferably at refluxing temperature of the solvent.

The reaction of the third process can be performed in a solvent such as acetic acid or hydrochloric acid, by reacting metallic zinc, zinc amalgam or zinc-copper alloy. The reaction can be performed at a reaction temperature of −10° C. to 100° C., preferably at 0° C. to room temperature.

The fourth process can be performed under acidic condition. For the acidic condition, hydrochloric acid, sulfuric acid, acetic acid, phosphoric acid or their mixtures, the mixed solvents of these acids with organic solvent such as sulfolane, or the like are used. The reaction can be performed at a reaction temperature of 0° C. to 150° C., preferably at refluxing temperature of the solvent.

The fifth process can be performed by leaving the carboxyl group as it is, or converting it to the reactive derivative.

In the case of the reaction using the reactive derivative, the reaction can be performed in a solvent such as methylene chloride, chloroform, dioxane or N,N-dimethylformamide in the presence or absence of, for example, alkali metal hydride such as sodium hydride, alkali metal hydroxide such as sodium hydroxide, alkali metal carbonate such as potassium carbonate, or organic base such as pyridine or triethylamine as a base.

In the case of conducting the reaction by leaving the carboxylic acid as it is, the reaction can be performed in a solvent such as methylene chloride, chloroform, dioxane or N,N-dimethylformamide in the presence of condensing agent in lthe presence or absence of base, and further in the presence or absence of additive.

As the condensing agent, for example, dicyclohexylcarbodiimide, 1-[3-(dimethylamino)propyl]-3-ethylcarbodiimide hydrochloride, diethyl cyanophosphate, diphenylphosphoric azide, carbonyldiimidazole or the like can be mentioned. As the base, for example, alkali metal hydroxide such as sodium hydroxide, alkali metal carbonate Namely, the compounds (1a), the bond mode of A portion being —NHCOCH$_2$— in the general formula (1), can be prepared as follows. (first process) 4-Methoxybenzaldehyde (2) was treated with ethyl 2-chloro-2-(methylthio)acetate in the presence of Lewis acid (Chem. Pharm. Bull., 1982, 30, 915) to obtain ethyl 2-methylthio-2-(5-formyl-2-methoxyphenyl)acetate (3). Then, reacting (second process) (3) with thiazolidine-2,4-dione in the presence of catalyst, and subsequent elimination (third process) of methylthio group of ethyl 2-methylthio-2-[5-[(2,4-dioxothiazolidin-5-ylidene)methyl]-2-methoxyphenyl]acetate (4), and hydrolysis (fourth process) of the ethyl ester portion of ethyl 2-[5-[(2,4-dioxothiazolidin-5-ylidene)methyl]-2-methoxyphenyl]acetate (5), to give 2-[5-[(2,4-dioxothiazolidin-5-ylidene)methyl]-2-methoxyphenyl] acetic acid (6). Then reacting (fifth process) (6) with compounds represented by the general formula (8)

(8)

[wherein B denotes a lower alkyl group with carbon atoms of 1 to 4, lower alkoxy group with carbon atoms of 1 to 3, halogen atom, trifluoromethyl group, trifluoromethoxy group, phenyl group which is unsubstituted or may have substituents, phenoxy group which is unsubstituted or may have substituents or benzyloxy group which is unsubstituted or may have substituents], and subsequent reduction (sixth process) of the double bond of the general formula (7) obtained such as potassium carbonate, or organic base such as pyridine or triethylamine can be mentioned. As the additive, N-hydroxybenzotriazole, N-hydroxysuccinimide, 3,4-dihydro-3-hydroxy-4-oxo-1,2,3-benzotriazine or the like can be mentioned. The reaction can be performed at the reaction temperature of −20° C. to 100° C., preferably at 0° C. to 50° C.

The sixth process can be performed at a hydrogen pressure of 98.1 kPa to 491 kPa in a solvent such as ethanol, methanol, tetrahydrofuran, ethyl acetate or N,N-dimethylformamide in the presence of metallic catalyst such as palladium on activated carbon, platinum on activated carbon, platinum oxide or rhodium on alumina. The reaction can be performed at a reaction temperature of 0° C. to 100° C., preferably at room temperature to 80° C.

Moreover, compounds, the bond mode of A portion being —NHCOCH$_2$— in the said general formula (1), can also be prepared, for example, through following processes (Scheme 2).

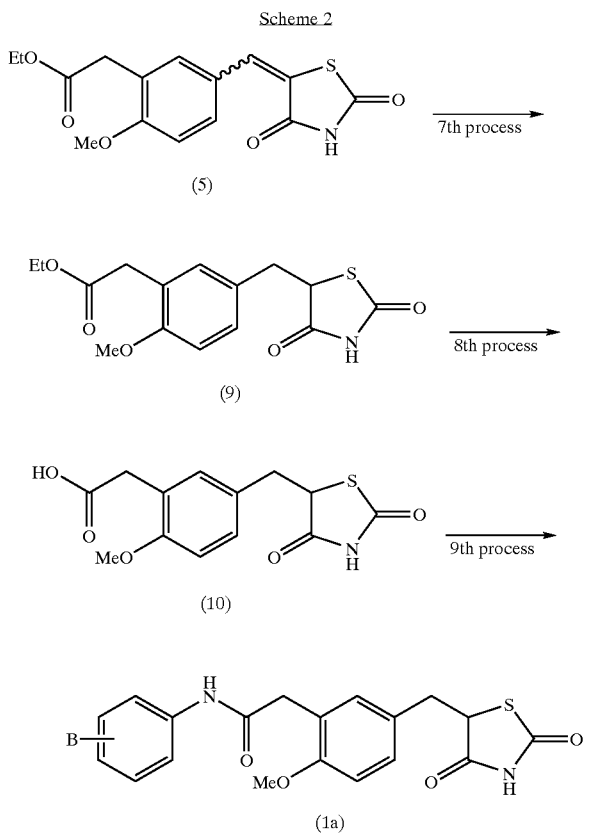

Namely, compounds (1a). the bond mode of A portion being —NHCOCH$_2$— in the general formula (1), can be prepared by reducing (seventh process) ethyl [5-[(2,4-dioxothiazolidin-5-ylidene)methyl]-2-methoxyphenyl] acetate (5) to obtain ethyl [5-[(2,4-dioxothiazolidin-5-yl) methyl]-2-methoxyphenyl]acetate (9). Then hydrolyzing (eighth process) (9) to obtain 2-[5-[(2,4-dioxothiazolidin-5-ylidene)methyl]-2-methoxyphenyl]acetic acid (10), and by reacting (ninth process) (10) with compounds represented by the general formula (8)

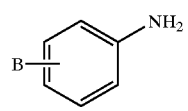

[wherein B denotes a lower alkyl group with carbon atoms of 1 to 4, lower alkoxy group with carbon atoms of 1 to 3, halogen atom, trifluoromethyl group, trifluoromethoxy group, phenyl group which is unsubstituted or may have substituents, phenoxy group which is unsubstituted or may have substituents or benzyloxy group which is unsubstituted or may have substituents].

The seventh process can be performed at a hydrogen pressure of 98.1 kPa to 491 kPa in a solvent such as ethanol, methanol, tetrahydrofuran, ethyl acetate or N,N-dimethylformamide in the presence of metallic catalyst such as palladium on carbon, platinum on carbon, platinum oxide or rhodium on alumina. The reaction can be performed at a reaction temperature of 0° C. to 100° C., preferably at room temperature to 80° C.

The hydrolysis of the eighth process can be performed under acidic condition. For the acidic condition, hydrochloric acid, sulfuric acid, acetic acid, phosphoric acid or their mixtures, the mixed solvents of these acids with organic solvent such as sulfolane, or the like are used. The reaction can be performed at a reaction temperature of 0° C. to 150° C., preferably at refluxing temperature of the solvent.

The reaction of the ninth process can be performed by leaving the carboxyl group as it is, or converting it to the reactive derivative.

In the case of the reaction using the reactive derivative, the reaction can be performed in a solvent such as methylene chloride, chloroform, dioxane or N,N-dimethylformamide in the presence or absence of, for example, alkali metal hydride such as sodium hydride, alkali metal hydroxide such as sodium hydroxide, alkali metal carbonate such as potassium carbonate, or organic base such as pyridine or triethylamine as a base.

In the case of conducting the reaction by leaving the carboxylic acid as it is, the reaction can be performed in a solvent such as methylene chloride, chloroform, dioxane or N,N-dimethylformamide in the presence of condensing agent in the presence or absence of base, and in the presence or absence of additive.

As the condensing agent, for example, dicyclohexylcarbodiimide, 1-[3-(dimethylamino)propyl]-3-ethylcarbodiimide hydrochloride, diethyl cyanophosphate, diphenylphosphoric azide, carbonylduimidazole or the like can be mentioned. As the base, for example, alkali metal hydroxide such as sodium hydroxide, alkali metal carbonate such as potassium carbonate, or organic base such as pyridine or triethylamine can be mentioned. As the additive, N-hydroxybenzotriazole, N-hydroxysuccinimide, 3,4-dihydro-3-hydroxy-4-oxo-1,2,3-benzotriazine or the like can be mentioned. The reaction can be performed at the reaction temperature of −20° C. to 100° C., preferably at 0° C. to 50° C.

Moreover, compounds, the bond mode of A portion being —NHCONH— (1b) or —CH$_2$CONH— (1c) in the general formula (1), can be prepared, for example, through the following processes (Scheme 3).

Scheme 3

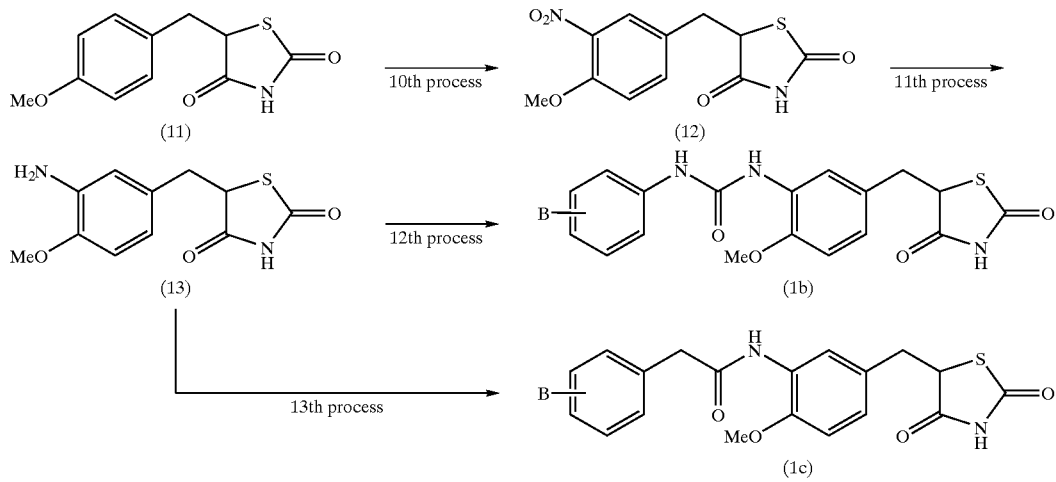

Namely, compounds, the bond mode of A portion being —NHCONH— (1b) or —CH$_2$CONH— (1c) in the general formula (1), can be prepared by nitrating (tenth process) 5-[(4-methoxyphenyl)methyl]thiazolidine-2,4-dione (11), then reducing (eleventh process) 5-[(4-methoxy-3-nitrophenyl)methyl]thiazolidine-2,4-dione (12) to give 5-[(3-amino-4-methoxyphenyl)methyl]thiazolidine-2,4-dione (13). Then by condensing (twelfth process, thirteenth process) (13) with compounds represented by the general formula (26)

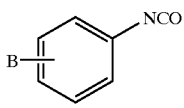

(26)

[wherein B denotes a lower alkyl group with carbon atoms of 1 to 4, lower alkoxy group with carbon atoms of 1 to 3, halogen atom, trifluoromethyl group, trifluoromethoxy group, phenyl group which is unsubstituted or may have substituents, phenoxy group which is unsubstituted or may have substituents or benzyloxy group which is unsubstituted or may have substituents], or with compounds represented by the general formula (27)

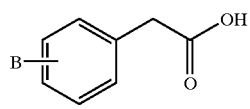

(27)

[wherein B denotes a lower alkyl group with carbon atoms of 1 to 4, lower alkoxy group with carbon atoms of 1 to 3, halogen atom, trifluoromethyl group, trifluoromethoxy group, phenyl group which is unsubstituted or may have substituents, phenoxy group which is unsubstituted or may have substituents or benzyloxy group which is unsubstituted or may have substituents].

The tenth process can be performed by reacting nitrating agent such as concentrated nitric acid, fuming nitric or the mixture of concentrated nitric acid with concentrated sulfuric acid (mixed acid) in a solvent such as methylene chloride or chloroform, or without solvent. The reaction can be performed at the reaction temperature of –20° C. to 120° C., preferably at 0° C. to 100° C.

The eleventh process can be performed by reduction at a hydrogen pressure of 98.1 kPa to 491 kPa in a solvent such as ethanol, ethyl acetate, tetrahydrofuran or N,N-dimethylformamide using a catalyst such as palladium on carbon, rhodium on alumina orplatinum oxide. The reaction can be performed at the reaction temperature of 0° C. to 100° C., preferably at room temperature to 80° C.

The twelfth process can be performed in a solvent such as ethyl acetate, tetrahydrofuran or N,N-dimethylformamide. The. reaction can be performed at the reaction temperature of –20° C. to 150° C., preferably at 0° C. to 100° C.

The thirteenth process can be performed by leaving carboxyl group as it is, or converting it to reactive derivative.

As the "reactive derivative of carboxyl group", acid chloride, acid bromide, acid anhydride, carbonylimidazole or the like can be mentioned. In the case of the reaction using reactive derivative, the reaction can be performed in a solvent such as dioxane or N,N-dimethylformamide in the presence or absence of, for example, alkali metal hydride such as sodium hydride, alkali metal hydroxide such as sodium hydroxide, alkali metal carbonate such as potassium carbonate, or organic base such as pyridine or triethylamine as a base.

In the case of conducting the reaction by leaving the carboxylic acid as it is, the reaction can be performed in a solvent such as methylene chloride, chloroform, dioxane or N,N-dimethylformamide in the presence of condensing agent in the presence or absence of base, and in the presence or absence of additive.

As the condensing agent, for example, dicyclohexylcarbodiimide, 1-[3-(dimethylamino)propyl]-3-ethylcarbodiimide hydrochloride, diethyl cyanophosphate, diphenylphosphoric azide, carbonyldiimidazole or the like can be mentioned. As the base, for example, alkali metal hydroxide such as sodium hydroxide, alkali metal carbonate such as potassium carbonate, or organic base such as pyridine or triethylamine can be mentioned. As the additive, N-hydroxybenzotriazole, N-hydroxysuccinimide, 3,4-dihydro-3-hydroxy-4-oxo-1,2,3-benzotriazine or the like can be mentioned. The reaction can be performed at the reaction temperature of –20° C. to 100° C. preferably at 0° C. to 50° C.

Moreover, compounds, the bond mode of A portion being —NHCONH— (1b) or —CH$_2$CONH— (1c) in the general formula (1), can also be prepared through following processes (Scheme 4).

Scheme 4

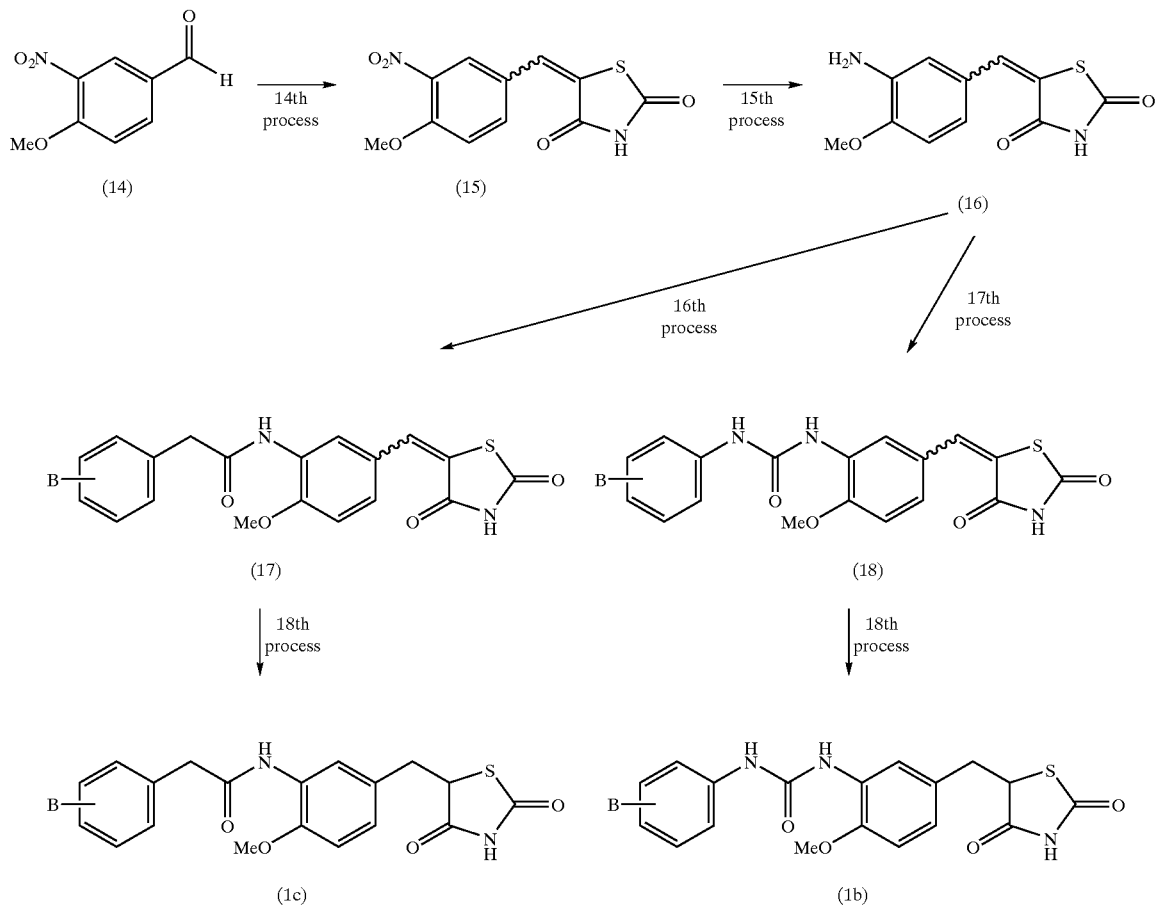

Namely, compounds, the bond mode of A portion being —NHCONH— (1b) or —CH₂CONH— (1c) in the general formula (1), can be prepared by reacting (fourteenth process) 4-methoxy-3-nitrobenzaldehyde (14) with thiazolidine-2,4-dione, then reducing (fifteenth process) the nitro group of 5-[(4-methoxy-3-nitrophenyl)methylidene]thiazolidine-2,4-dione (15) to give 5-[(3-amino-4-methoxyphenyl)methylidene]thiazolidine-2,4-dione (16), and condensing (sixteenth process, seventeenth process) (16) with the compounds represented by the general formula (27)

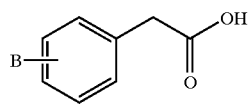

(27)

[wherein B denotes a lower alkyl group with carbon atoms of 1 to 4, lower alkoxy group with carbon atoms of 1 to 3, halogen atom, trifluoromethyl group, trifluoromethoxy group, phenyl group which is unsubstituted or may have substituents, phenoxy group which is unsubstituted or may have substituents or benzyloxy group which is unsubstituted or may have substituents], or with the compounds represented by the general formula (26)

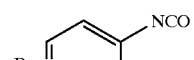

[wherein B denotes a lower alkyl group with carbon atoms of 1 to 4, lower alkoxy group with carbon atoms of 1 to 3, halogen atom, trifluoromethyl group, trifluoromethoxy group, phenyl group which is unsubstituted or may have substituents, phenoxy group which is unsubstituted or may have substituents or benzyloxy group which is unsubstituted or may have substituents], and by reducing (eighteenth process) the double bond of compounds represented by the general formula (17)

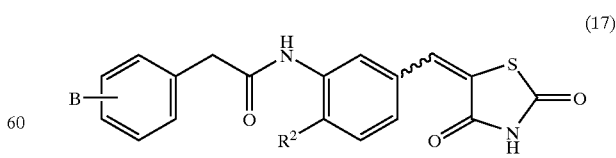

[wherein B denotes a lower alkyl group with carbon atoms of 1 to 4, lower alkoxy group with carbon atoms of 1 to 3, halogen atom, trifluoromethyl group, trifluoromethoxy group, phenyl group which is unsubstituted or may have substituents, phenoxy group which is unsubstituted or may have substituents or benzyloxy group which is unsubstituted or may have substituents], or the general formula (18)

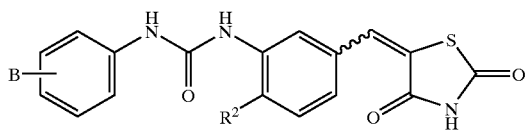

(18)

[wherein B denotes a lower alkyl group with carbon atoms of 1 to 4, lower alkoxy group with carbon atoms of 1 to 3, halogen atom, trifluoromethyl group, trifluoromethoxy group, phenyl group which is unsubstituted or may have substituents, phenoxy group which is unsubstituted or may have substituents or benzyloxy group which is unsubstituted or may have substituents].

The fourteenth process can be performed in a solvent such as benzene, toluene, xylene or acetic acid, or without solvent. As the catalyst, secondary amine such as piperidine or pyrrolidine, or ammonium acetate can be used. The reaction can be performed at the reaction temperature of 0° C. to 150° C., preferably at refluxing temperature of the solvent.

The fifteenth process can be performed by reducing in a mixed solvent of alcohol such as ethanol or methanol with hydrochloric acid, using tin, tin chloride(II), tin amalgam or the like. The reaction can be performed at the reaction temperature of 0° C. to 100° C., preferably at room temperature to 50° C.

The sixteenth process can be performed by leaving the carboxyl group as it is, or converting it to the reactive derivative.

In the case of the reaction using the reactive derivative, the reaction can be performed in a solvent such as dioxane or N,N-dimethylformamide in the presence or absence of, for example, alkali metal hydride such as sodium hydride, alkali metal hydroxide such as sodium hydroxide, alkali metal carbonate such as potassium carbonate, or organic base such as pyridine or triethylamine as a base.

In the case of conducting the reaction by leaving the carboxylic acid form as it is, the reaction can be performed in a solvent such as methylene chloride, chloroform, dioxane or N,N-dimethylformamide in the presence of condensing agent in the presence or absence of base, and in the presence or absence of additive.

As the condensing agent, for example, dicyclohexylcarbodiimide, 1-[3-(dimethylamino)propyl]-3-ethylcarbodiimide hydrochloride, diethyl cyanophosphate, diphenylphosphoric azide, carbonyldiimidazole or the like can be mentioned. As the base, for example, alkali metal hydroxide such as sodium hydroxide, alkali metal carbonate such as potassium carbonate, or organic base such as pyridine or triethylamine can be mentioned. As the additive, N-hydroxybenzotriazole, N-hydroxysuccinimide, 3,4-dihydro-3-hydroxy-4-oxo-1,2,3-benzotriazine or the like can be mentioned. The reaction can be performed at the reaction temperature of −20° C. to 100° C., preferably at 0° C. to 50° C.

The seventeenth process can be performed in a solvent such as ethyl acetate, tetrahydrofuran or N,N-dimethylformamide. The reaction can be performed at the reaction temperature of −20° C. to 150° C., preferably at 0° C. to 100° C.

The eighteenth process can be performed at a hydrogen pressure of 98.1 kPa to 491 kPa in a solvent such as ethanol, methanol, tetrahydrofuran, ethyl acetate or N,N-dimethylformamide in the presence of metallic catalyst such as palladium on carbon, platinum on carbon, platinum oxide or rhodium on alumina. The reaction can be performed at the reaction temperature of 0° C. to 100° C., preferably at room temperature to 80° C.

Moreover, compounds, the bond mode of A portion being —CH$_2$CH$_2$CO— (1d) in the general formula (1), can be prepared, for example, through following processes (Scheme 5).

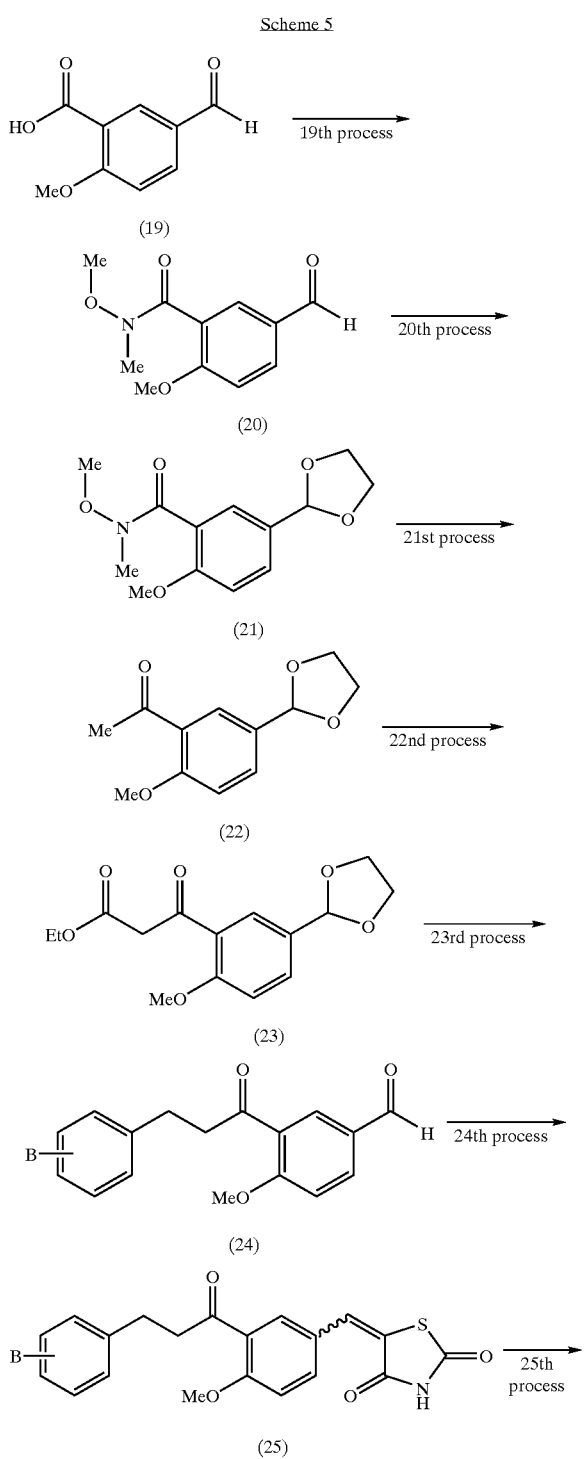

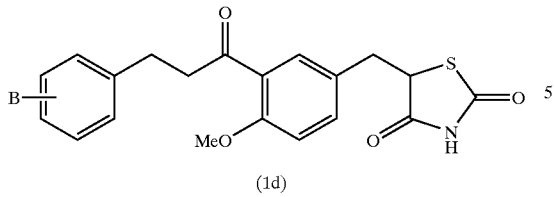

(1d)

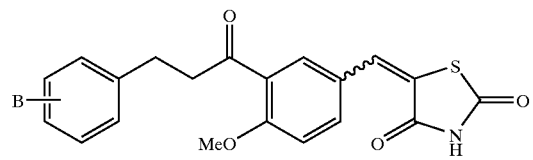

(25)

Namely, compounds, the bond mode of A portion being —CH$_2$CH$_2$CO— (1d) in the general formula (1), can be prepared by reacting (nineteenth process) publicly known [Japanese Unexamined Patent Publication No. Hei 1-316363[ 5-formyl-2-methoxybenzoic acid (19) with N,O-dimethylhydroxylamine, then protecting (twentieth process) formyl group of N-methoxy-N-methyl-5-formyl-2-methoxybenzamide (20) with ethylene glycol to obtain N-methoxy-N-methyl-5-(1,3-dioxolane-2-yl)-2-methoxybenzamide (21). Then reacting (twenty-first process) (21) with magnesium methyl iodide, and reacting (twenty-second process) 3'-(1,3-dioxolane-2-yl)-2'-methoxyacetophenone (22) with diethyl carbonate in the presence of base, then reacting (twenty-third process) ethyl 3-[5-(1,3-dioxolane-2-yl)-2-methoxy- phenyl]-3-oxopropionate (23) with the compounds represented by the general formula (28)

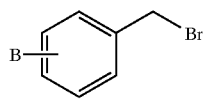

(28)

[wherein B denotes a lower alkyl group with carbon atoms of 1 to 4, lower alkoxy group with carbon atoms of 1 to 3, halogen atom, trifluoromethyl group, trifluoromethoxy group, phenyl group which is unsubstituted or may have substituents, phenoxy group which is unsubstituted or may have substituents or benzyloxy group which is unsubstituted or may have substituents], in the presence of base, followed by decarbonation reaction, to obtain compounds represented by a general formula (24)

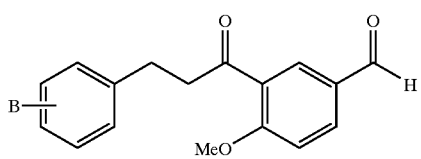

(24)

[wherein B denotes a lower alkyl group with carbon atoms of 1 to 4, lower alkoxy group with carbon atoms of 1 to 3, halogen atom, trifluoromethyl group, trifluoromethoxy group, phenyl group which is unsubstituted or may have substituents, phenoxy group which is unsubstituted or may have substituents or benzyloxy group which is unsubstituted or may have substituents]. Then reacting (twenty-fourth process) (24) with thiazolidine-2,4-dione in the presence of catalyst to obtain the compounds represented by the general formula (25)

[wherein B denotes a lower alkyl group with carbon atoms of 1 to 4, lower alkoxy group with carbon atoms of 1 to 3, halogen atom, trifluoromethyl group, trifluoromethoxy group, phenyl group which is unsubstituted or may have substituents, phenoxy group which is unsubstituted or may have substituents or benzyloxy group which is unsubstituted or may have substituents], and by reducing (twenty-fifth process) the double bond of these compounds.

The nineteenth process can be performed by leaving carboxyl group as it is, or converting it to reactive derivative.

In the case of the reaction using the reactive derivative, the reaction can be performed in a solvent such as dioxane or N,N-dimethylformamide in the presence or absence of, for example, alkali metal hydride such as sodium hydride, alkali metal hydroxide such as sodium hydroxide, alkali metal carbonate such as potassium carbonate, or organic base such as pyridine or triethylamine as a base.

In the case of conducting the reaction by leaving the carboxylic acid as it is, the reaction can be performed in a solvent such as methylene chloride, chloroform, dioxane or N,N-dimethylformamide in the presence of condensing agent in the presence or absence of base, and in the presence or absence of additive.

As the condensing agent, for example, dicyclohexylcarbodiimide, 1-[3-(dimethylamino)propyl]-3-ethylcarbodiimide hydrochloride, diethyl cyanophosphate, diphenylphosphoric azide, carbonyldiimidazole or the like can be mentioned. As the base, for example, alkali metal hydroxide such as sodium hydroxide, alkali metal carbonate such as potassium carbonate, or organic base such as pyridine or triethylamine can be mentioned. As the additive, N-hydroxybenzotriazole, N-hydroxysuccinimide, 3,4-dihydro-3-hydroxy-4-oxo-1,2,3-benzotriazine or the like can be mentioned. The reaction can be performed at the reaction temperature of −20° C. to 100° C., preferably at 0° C. to 50° C.

The twentieth process can be performed in a solvent such as benzene, toluene or xylene in the presence of acid catalyst. As the acid catalyst, sulfuric acid, p-toluenesulfonic acid, camphorsulfonic acid, phosphorus oxychloride, oxalic acid or the like can be used. The reaction can be performed at the reaction temperature of 0° C. to 150° C., preferably at refluxing temperature of solvent.

The twenty-first process can be performed in a solvent such as ether, tetrahydrofuran or dioxane. The reaction can be performed at the reaction temperature of −100° C. to room temperature, preferably at −80° C. to 0° C.

The twenty-second process can be performed in a solvent such as ether, tetrahydrofuran or dioxane in the presence of base. As the base, for example, alkali metal hydride such as sodium hydride, organometallic compound such as butyl lithium, metal amide such as lithium diisopropylamide, or metal alkoxide such as sodium methoxide or potassium t-butoxide can be used. The reaction can be performed at the reaction temperature of −20° C. to 150° C., preferably at 0° C. to 50° C.

For the twenty-third process, first, the alkylating reaction can be performed in a solvent such as ether, tetrahydrofuran or dioxane in the presence of base. As the base, for example, alkali metal hydride such as sodium hydride, organometallic compound such as butyl lithium, metal amide such as lithium diisopropylamide, or metal alkoxide such as sodium methoxide or potassium t-butoxide can be used. The reaction can be performed at the reaction temperature of −20° C. to 150° C., preferably at refluxing temperature of the solvent. Following decarbonation reaction can be performed under acidic condition. As the acid, hydrochloric acid, acetic acid, sulfuric acid, phosphoric acid or the like singly, or mixed solvents thereof can be used. The reaction can be performed at the reaction temperature of room temperature to 150° C., preferably at refluxing temperature of the solvent.

The twenty-fourth process can be performed in a solvent such as benzene, toluene, xylene, ethanol or acetic acid, or without solvent. As the catalyst, secondary amine such as piperidine or pyrrolidine, or ammonium acetate can be used.

The reaction can be performed at the reaction temperature of 0° C. to 150° C., preferably at refluxing temperature of the solvent.

The twenty-fifth process can be performed at a hydrogen pressure of 98.1 kPa to 491 kPa in a solvent such as ethanol, methanol, tetrahydrofuran, ethyl acetate or N,N-dimethylformamide in the presence of metal catalyst such as palladium on carbon, platinum on carbon, platinum oxide or rhodium on alumina. The reaction can be performed at the reaction temperature of 0° C. to 100° C., preferably at room temperature to 80° C.

As the administering form of the novel compounds of the invention, for example, oral administration with tablet, capsule, granule, powder, inhalant, syrup or the like, or parenteral administration with injection, suppository or the like can be mentioned.

Best embodiment to put the invention into practice

In following, the invention will be illustrated based on examples, but the invention is not confined to these examples.

EXAMPLE 1

Ethyl 2-Methylthio-2-(5-formyl-2-methoyphenyl) acetate

Under an atmosphere of argon, to a solution of 4-methoxybenzaldehyde (8.17 g, 60.0 mmol) in methylene chloride (250 mL) was added dropwise anhydrous tin chloride(IV) (7.02 mL, 60.0 mmol) under cooling with ice and stirring. After stirring for 10 minutes at room temperature, a solution of ethyl 2-chloro-2-(methylthio) acetate (10.2 g, 60.5 mmol), methylene chloride (50 mL) and carbon tetrachloride (50 mL) was added dropwise. After refluxing for 16 hours, the reaction mixture was allowed to stand for cooling, poured into ice-water, and the organic layer was separated, the aqueous layer was then extracted with methylene chloride. After combined respective organic layers, they were washed with water, saturated aqueous solution of sodium hydrogen-carbonate and saturated brine in sequence, then dried over anhydrous sodium sulfate and concentrated. The residue was purified by silica gel chromatography (eluate n-hexane:ethyl acetate=6:1 v/v) to obtain 7.51 g (47%) of the title compound as a yellow oily product.

Mass analysis (EI$^+$) (m/z): 268 (M$^+$).

EXAMPLE 2

Ethyl 2-Methylthio-2-[5-[(2,4-dioxothiazolidin-5-ylidene)methyl]-2-methoxyphenyl]acetate Ethyl 2-methylthio-2-(5-formyl-2-methoxyphenyl) acetate (7.50 g, 28.0 mmol), thiazolidine-2,4-dione (3.94 g, 33.6 mmol), piperidine (2.80 mL, 28.3 mmol) and ethanol (100 mL) were mixed and refluxed for 14 hours. After allowed to stand for cooling, concentrated hydrochloric acid was added under cooling with ice and stirring to make the reaction mixture acidic. Ice water was added thereto and the mixture was stirred for 30 minutes. The precipitated crystals were collected by filtration, washed with ethanol and water, and then dried to obtain 6.18 g (60%) of the title compound as yellow crystals.

Mass analysis (EI$^+$) (m/z): 367 (M$^+$).

EXAMPLE 3

Ethyl 2-[5-[(2,4-Dioxothiazolidin-5-ylidene) methyl]-2-methoxyphenyl]acetate

Ethyl 2-methylthio-2-[5-[(2,4-dioxothiazolidin-5-ylidene)methyl]-2-methoxyphenyl]acetate (6.18 g, 16.8 mmol) and acetic acid (100 mL) were mixed, and zinc powder (46.0 g, 706 mmol) was added under stirring, which was stirred for 24 hours at room temperature. Zinc was collected by filtration. washed with acetic acid, and the filtrate was concentrated. The residue was dissolved into ethyl acetate, washed with water and brine in sequence, then dried over anhydrous sodium sulfate and concentrated. The residue was recrystallized from methanol to obtain 2.71 g (50%) of the title compound as yellow powder.

Mass analysis (EI$^+$) (m/z): 321 (M$^+$).

EXAMPLE 4

2-[5-[(2,4-Dioxothiazolidin-5-ylidene)methyl]-2-methoxyphenyl]-acetic Acid

Ethyl 2-[5-[(2,4-dioxothiazolidin-5-ylidene)methyl]-2-methoxyphenyl]acetate (1.29 g, 4.01 mmol), concentrated hydrochloric acid (20 mL)and acetic acid (20 mL) were mixed and refluxed for 2.5 hours. After allowed to stand for cooling, ice water was added thereto and the precipitated crystals were collected by filtration, washed with water, and then dried to obtain 1.13 g (96%) of title compound as yellow powder.

Mass analysis (EI$^+$) (m/z): 293 (M$^+$).

EXAMPLE 5

N-[4-(Trifluoromethyl)phenyl]-2-[5-[(2,4-dioxothiazolidin-5-ylidene)methyl]-2-methoxyphenyl]acetamide 2-[5-[(2,4-Dioxothiazolidin-5-ylidene)methyl]-2-methoxyphenyl]-acetic acid (440 mg, 1.50 mmol), 4-(trifluoromethyl)aniline (242 μL, 1.50 mmol), triethylamine (210 μL, 1.51 mmol) and dehydrated N,N-dimethylformamide (5 mL) were mixed, and, under an atmosphere of argon, diethyl cyanophosphate (228 μL, 1.50 mmol) was added under cooling with ice and stirring. After stirring for 1 hour at room temperature, the mixture was allowed to stand for 3 days. The reaction mixture was poured into ice water and the precipitated crystals were collected by filtration. The crystals were washed with ethyl acetate, and then dried to obtain 472 mg (72%) of the title compound as yellow crystals.

Mass analysis (EI$^+$) (m/z): 436 (M$^+$).

EXAMPLE 6

N-[4-(Trifloromethyl)phenyl]-2-[5-[(2,4-dioxothiazolidin-5-yl)methyl]2-methoxyphenyl] acetamide N-[4-(Trifluoromethyl)phenyl]-2-[5-((2,4-dioxothiazolidin-5-ylidene)methyl]-2-methoxyphenyl]

acetamide (300 mg, 0.687 mmol), 10% palladium on carbon (300 mg) and a mixed solvent of tetrahydrofuran and ethanol (2:1 v/v, 40 mL) were mixed, and hydrogenation was performed at room temperature and at an initial pressure of 392 kPa. After completion of the reaction, catalyst was filtered and the filtrate was concentrated. The residue was purified by silica gel chromatography (eluate n-hexane:ethyl acetate=2:1 v/v) to obtain 172 mg (57%) of the title compound as colorless powder.

Melting point 194.5–196.5° C.;

Mass analysis (EI$^+$) (m/z): 438 (M$^+$);

Elemental analysis (%) $C_{20}H_{17}F_3N_2O_4S$: Calcd. (%) C, 54.79; H, 3.91; N, 6.39. Found (%) C, 54.62; H, 3.81; N, 6.24.

EXAMPLE 7

5-[(4-Methoxyphenyl)methylidene]thiazolidine-2,4-dione

4-Methoxybenzaldehyde (20.4 g, 150 mmol), thiazolidine-2,4-dione (21.1 g, 180 mmol), piperidine (12.8 g, 150 mmol) and ethanol (150 mL) were mixed and refluxed for 18 hours. After allowed to stand for cooling, the precipitated crystals were collected by filtration. These were washed with ethanol, and then dried to obtain 11.2 g (32%) of the title compound as yellow crystals. Moreover, the filtrate was made acidic with concentrated hydrochloric acid, and the precipitated crystals were collected by filtration, washed with ethanol and water, and then dried to additionally obtain 18.1 g (51%, totally 83%) of the title compound as yellow crystals.

Mass analysis (EI$^+$) (m/z): 235 (M$^+$).

EXAMPLE 8

5-[(4-Methoxyphenyl)methyl]thiazolidine-2,4-dione

5-[(4-Methoxyphenyl)methylidene]thiazolidine-2,4-dione (6.00 g, 25.5 mmol), 10% palladium on carbon (6.00 g) and a mixed solvent of tetrahydrofuran and ethanol (2:1 v/v, 300 mL) were mixed, and hydrogenation was performed at room temperature and at an initial pressure of 294 kPa. After completion of the reaction, catalyst was filtered and the filtrate was concentrated. The residue was purified by silica gel chromatography (eluate n-hexane: ethyl acetate= 2:1 v/v) to obtain 5.84 g (97%) of the title compound as colorless powder.

Mass analysis (EI$^+$) (m/z): 237 (M$^+$).

EXAMPLE 9

5-[(4-Methoxy-3-nttrophenyl)methyl]thiazolidine-2,4-dione

To concentrated nitric acid (100 mL) was added 5-[(4-methoxyphenyl)methyl]thiazolidine-2,4-dione (3.56 g, 15.0 mmol) little by little under cooling with ice-salt and stirring. After stirring further for 3 hours, the reaction mixture was poured into ice water, and the precipitated crystals were collected by filtration, washed with water, and then dried to obtain 3.04 g (72%) of the title compound as yellow crystals.

Mass analysis (EI$^+$) (m/z): 282 (M$^+$).

EXAMPLE 10

5-[3-Amino-4-methoxyphenyl)methyl]thiazolidine-2,4-dione

5-[(4-Methoxy-3-nitrophenyl)methyl]thiazolidine-2,4-dione (3.00 g, 10.6 mmol), 10% palladium on carbon (2.00 g) and a mixed solvent of ethyl acetate and ethanol (1:1 v/v, 200 mL) were mixed, and hydrogenation was performed at room temperature and at an initial pressure of 294 kPa. After completion of the reaction, catalyst was filtered and the filtrate was concentrated. The residue was purified by silica gel chromatography (eluate n-hexane: ethyl acetate=1:1 v/v) to obtain 2.55 g (95%) of the title compound as light brown crystals.

Mass analysis (EI$^+$) (m/z): 252 (M$^+$).

EXAMPLE 11

5-[[4-Methoxy-3-[3-[4-(trifluoromethyl)phenyl]ureido]phenyl]methyl]thiazolidinex-2,4-dione 5-[(3-Amino-4-methoxyphenyl)methyl]thiazolidine-2,4-dione (378 mg, 1.50 mmol) and dehydrated tetrahydrofuran (5 mL) were mixed and under an atmosphere of argon, 4-trifluoromethyl-isocyanate (0.236 mL, 1.65 mmol) was added at room temperature under stirring, and stirred for 6 hours at room temperature. After allowed to stand overnight, the reaction mixture was concentrated, and the residue was recrystallized from methylene chloride to obtain 375 mg (57%) of the title compound as colorless powder.

Melting point 202.0–204.0° C.;

Mass analysis (EI$^+$) (m/z): 439 (M$^+$);

Elemental analysis (%) $C_{19}H_{16}F_3N_3O_4S$: Calcd. (%) C, 51.93; H, 3.67; N, 9.56. Found (%) C, 51.80; H, 3.60; N, 9.58.

EXAMPLE 12

5-[(4-Methoxy-3-nitrophenyl)methylidene]thiazolidine-2,4-dione

4-Methoxy-3-nitrobenzaldehyde (4.00 g, 22.2 mmol), thiazolidine-2,4-dione (3.10 g, 26.5 mmol), ammonium acetate (3.40 g, 44.1 mmol), acetic acid (8 mL) and benzene (120 mL) were mixed, and, while removing water formed by the reaction, the mixture was refluxed for 8 hours. After allowed to stand for cooling, the precipitated crystals were collected by filtration, washed with benzene and 20% aqueous acetone, and then dried to obtain 5.50 g (88%) of the title compound as yellow powder.

Mass analysis (EI$^+$) (m/z): 280 (M$^+$).

EXAMPLE 13

5-[(3-Amino-4-methoxyphenyl)methylidene]thiazolidine-2,4-dione

5-[(4-Methoxy-3-nitrophenyl)methylidene]thiazolidine-2,4-dione (841 mg, 3.00 mmol), ethanol (20 mL) and concentrated hydrochloric acid (10 mL) were mixed, and tin chloride(II) dihydrate (2.26 g, 9.01 mmol) was added little by little at room temperature under stirring. After stirring for 8 hours at room temperature, the reaction mixture was poured into water and neutralized with saturated aqueous sodium hydrogencarbonate, which was extracted with ethyl acetate. The extracted solution was washed with water, then dried over anhydrous sodium sulfate and concentrated to obtain 641 mg (85%) of the title compound as yellowish orange powder.

Mass analysis (EI$^+$) (m/z): 250 (M$^+$).

EXAMPLE 14

N-[2-Methoxy-5-[(2,4-dixothiazolidin-5-ylidene)methyl]phenyl]-2-[4-(trifluoromethyl)phenyl]-acetamide 5-[(3-Amino-4-methoxyphenyl)methylidene]thiazolidine-2,4-dione (561 mg, 2.24 mmol), 4-(trifluoromethyl)phenylacetic acid (460 mg, 2.25 mmol) and N,N-dimethylformamide (6 mL) were mixed, and, under an atmosphere of argon, triethylamine (250 mg, 2.46 mmol) and diethyl cyanophosphate (0.37 mL, 2.44 mmol) were added under cooling with ice and stirring. After stirring further for 20 minutes under cooling with ice, the mixture was stirred for 6 hours at room temperature. The reaction mixture was poured into ice water and the precipitated crystals were collected by filtration. The crystals were washed with water, and then dried to obtain 873 mg (89%) of title compound as yellow powder.

Mass analysis (EI$^+$) (m/z): 436 (M$^+$).

EXAMPLE 15

N-[2-Methoxy-5-[(2,4-dioxothiazolidin-5-yl)methyl]phenyl]-2-[4-(trifluoromethyl)phenyl]acetamide N-[2-Methoxy-5-[(2,4-dioxothiazolidin-5-ylidene)methyl]-phenyl]-2-[4-(trifyluoromethyl)phenyl]acetamide (610 mg, 1.40 mmol), 10% palladium-carrying activated carbon (600 mg) and a mixed solvent of ethyl acetate with ethanol (1:1 v/v, 150 mL) were mixed, and hydrogenation was performed at room temperature and at an initial pressure of 343 kPa. After completion of the reaction, catalyst was filtered and the filtrate was concentrated. The residue was recrystallized from ether to obtain 598 mg (98%) of the title compound as colorless fine powder.

Melting point 147.0–149.0° C.;

Mass analysis (EI$^+$) (m/z): 438 (M$^+$);

Elemental analysis (%) $C_{20}H_{17}F_3N_2O_4S$: Calcd.(%) C, 54.79; H, 3.91; N, 6.39. Found (%) C, 54.71; H, 3.88; N, 6.33.

EXAMPLE 16

N-Methoxy-N-methyl-5-formyl-2-methozybenzamide

Publicly known [Japanese Unexamined Patent Publication No. Hei 1-316363] 5-formyl-2-methoxybenzoic acid (6.70 g, 37.2 mmol), triethylamine (13.0 mL, 93.3 mmol) and dichloromethane (200 mL) were mixed and ethyl chlorocarbonate (3.90 mL, 40.8 mmol) was added under cooling with ice and stirring, which was stirred for 20 minutes. Next, N,O-dimethylhydroxylamineehydrochloride (4.35 g. 44.6 mmol) was added, and the mixture was stirred for 6 hours at room temperature, which was then allowed to stand overnight. After washed the reaction mixture with lmol/L hydrochloric acid, water, saturated aqueous solution of sodium hydrogencarbonate and water in sequence, the organic layer was separated, then dried over anhydrous sodium sulfate and concentrated. The residue was purified by silica gel chromatography (eluate n-hexaneethyl acetate=2:3 v/v) to obtain 6.56 g (79%) of the title compound as colorless crystals.

Mass analysis (EI$^+$) (m/z): 223 (M$^+$).

EXAMPLE 17

N-Methoxy-N-methyl-5-(1,3-dioxolan-2-yl)-2-methoxybenzamide

N-Methoxy-N-methyl-5-formyl-2-methoxybenzamide (6.56 g, 29.4 mnmol), ethylene glycol (8.20 mL, 147 mmol), p-toluenesulfonic acid monohydrate (110 mg, 0.578 mmol) and toluene (100 mL) were mixed, and, while removing water generated using dean-stark apparatus, the mixture was refluxed for 4 hours. After allowed to stand for cooling, ethyl acetate was added, which was washed with saturated aqueous solution of sodium hydrogencarbonate and water in sequence. Then, the organic layer was dried over anhydrous sodium sulfate and concentrated. The residue was purified by silica gel chromatography (eluate n-hexane:ethyl acetate=1:2 v/v) to obtain 6.60 g (84%) of the title compound as a colorless oil.

Mass analysis (EI$^+$) (m/z): 267 (M$^+$).

EXAMPLE 18

5'-(1,3-Dioxolan-2-yl)-2'-methoxyacetophenone

N-Methoxy-N-methyl-5-(1,3-dioxolan-2-yl)-2-methoxybenzamide (6.60 g, 24.7 mmol) and dehydrated tetrahydrofuran (200 mL) were mixed, and under an atmosphere of argon, the mixture was cooled using dry ice-acetone bath, and 3.0 mol/L solution of methyl magnesium iodide in ether (24.7 mL, 74.1 mmol) was added dropwise slowly under stirring. After completion of the dropwise addition, the mixture was stirred for 1.5 hours under cooling with ice. A saturated aqueous solution of ammonium chloride (200 mL) was added dropwise thereto under cooling with ice and stirring. After separated the organic layer, the aqueous layerwas extracted with ethyl acetate. Respective organic layers were combined, washed with water and saturated brine in sequence, then dried over anhydrous sodium sulfate and concentrated. The residue was purified by silica gel chromatography (eluate n-hexane:ethyl acetate=4:1 v/v) to obtain 4.31 g (79%) of the title compound as colorless crystals.

Mass analysis (EI$^+$) (m/z): 267 (M+H)$^+$.

EXAMPLE 19

Ethyl 3-[5-(1,3-dioxolan-2-yl)-2-methoxyphenyl]-3-oxopropionate

To dehydrated ether (15 mL) was added sodium hydride (940 mg, 23.5 mmol) under cooling with ice and stirring, and following this, diethyl carbonate (1.66 g, 14.1 mmol) was added, which was stirred for 30 minutes at room temperature. Next, 5'-(1,3-dioxolane-2-yl)-2'-methoxyacetophenone (2.08 g, 9.36 mmol), dehydrated tetrahydrofuran (20 mL) and ethanol (0.05 mL) were mixed and added dropwise slowly. After completion of the dropwise addition, the mixture was refluxed for 7 hours. After allowed to stand for cooling, the reaction mixture was poured slowly into a solution of 2 mol/L hydrochloric acid (20 mL) and ethyl acetate (30 mL) under cooling with ice and stirring. After separated the organic layer, the aqueous layer was extracted with ethyl acetate. Respective organic layers were combined, washed with water and saturated brine in sequence, then dried over anhydrous sodium sulfate and concentrated. The residue was purified by silica gel chromatography (eluate n-hexane:ethyl acetate=3:1 v/v) to obtain 1.44 g (52%) of the title compound as a pale yellow oil.

Mass analysis (EI$^+$) (m/z): 267 (M+H)$^+$.

EXAMPLE 20

3-[4-(Trlfluoromethyl)phenyl]-1-(5-formyl-2-methoxvphenyl)propan-1-one

To dehydrated tetrahydrofuran (7 mL) was added sodium hydride (190 mg, 4.75 mmol), and, under an atmosphere of argon, a solution of ethyl 3-[5-(1,3-dioxolane-2-yl)-2-methoxyphenyl]-3-oxopropionate (1.40 g, 4.76 mmol) dissolved into dehydrated tetrahydrofuran (10 mL) was added dropwise slowly under cooling with ice and stirring. After stirring for 30 minutes at room temperature, a solution of 4-(trifluoromethyl)benzyl bromide (1.30 g, 4.44 mmol) dissolved into dehydrated tetrahydrofuran (3 mL) was added dropwise. After completion of the dropwise addition, the mixture was refluxed for 18 hours. After allowed to stand for cooling, the reaction mixture was concentrated. Concentrated hydrochloric acid (3 mL) and acetic acid (10 mL) were added thereto, and the mixture was refluxed for 5 hours. After allowed to stand for cooling, the reaction mixture was poured into ice water, which was extracted with ethyl acetate. The extracted solution was washed with saturated aqueous solution of sodium hydrogen-carbonate, water and brine in sequence, then dried over anhydrous sodium sulfate and concentrated. The residue was purified by silica gel chromatography (eluate n-hexane: ethyl acetate=6:1 v/v) to obtain 911 mg (61%) of the title compound as colorless crystals.

Mass analysis (EI$^+$) (m/z): 336 (M$^+$).

EXAMPLE 21

5-[[3-[3-[4-(Trifluoromethyl)phenyl]propanoyl]-4-methoxyphenyl]methylidene]thiazolidlne-2,4-dione 3-[4-(Trifluoromethyl)phenyl]-1-(5-formyl-2-methoxyphenyl)propane-1-one (900 mg, 2.68 mmol), 1,3-thiazolidine-2,4-dione (377 mg, 3.21 mmol), piperidine (265 μL, 2.68 mmol) and ethanol (10 mL) were mixed, and the mixture was refluxed for 13 hours. After allowed to stand for cooling, this was made acidic with concentrated hydrochloric acid under cooling with ice and stirring, and the precipitated crystals were collected by filtration. These were washed with ethanol and water, and then dried to obtain 906 mg (78%) of the title compound as yellow crystals.

Mass analysis (EI$^+$) (m/z): 435 (M$^+$).

EXAMPLE 22

5-[[3-[3-[4-(Trifluoromethyl)phenyl]propanoyl]-4-methoxynhenyl]methyl]thiazolidine-2,4-dione 5-[[3-[3-[4-(Trifluoromethyl)phenyl]propanoyl]-4-methoxyphenyl]methylidene]-1,3-thiazolidine-2,4-dione (500 mg, 1.15 mmol), 10% palladium on carbon (500 mg) and tetrahydrofuran (50 mL) were mixed, and medium pressure hydrogenation was performed for 8 hours at an initial pressure of 392 kPa. After completion of the reaction, the catalyst was filtered, the filtrate was concentrated, and the residue was purified by silica gel chromatography (eluate n-hexane:ethyl acetate=2:1 v/v) to obtain 444 mg (88%) of the title compound as colorless powder.

Melting point 103.0–104.5° C.;
Mass analysis (EI$^+$) (m/z): 437 (M$^+$);
Elemental analysis (%) $C_{21}H_{18}F_3NO_4S$: Calcd. (%) C, 57.66; H, 4.15; N, 3.20. Found (%) C, 57.84; H, 4.10; N, 3.25.

EXAMPLE 23

N-[4-(Phenoxy)phenyl]-2-[5-[(2,4-dioxothiazolidin-5-yl)methyl]-2-methoxyphenyl]acetamide Similarly to Example 6, the title compound was obtained as colorless powder.

Melting point 82.0–84.0° C.;
Mass analysis (EI$^+$) (m/z): 462 (M$^+$);
Elemental analysis (%) $C_{25}H_{22}N_2O_5S.1H_2O$: Calcd. (%) C, 62.49; H, 5.03; N, 5.83. Found (%) C, 62.21; H, 4.94; N, 6.07.

EXAMPLES 24 THROUGH 26

Similarly to Example 11, the compounds in Table 1 were obtained.

TABLE 1

| Example | A | B | Melting point (° C.) | Charac. formula | Elemental analysis (%) |
|---|---|---|---|---|---|
| 24 | NHCONH | 4-Me | 171.5–172.5 | $C_{19}H_{19}N_3O_4S$ | Calc.; C 59.21, H 4.97, N 10.90<br>Found; C 59.41, H 4.95, N 10.84 |
| 25 | NHCONH | 4-Cl | 236.0–238.0 | $C_{18}H_{16}ClN_3O_4S$ | Calc.; C 53.27, H 3.97, N 10.35<br>Found; C 53.66, H 3.83, N 10.11 |
| 26 | NHCONH | 4-OC$_2$H$_5$ | 195.0–197.0 | $C_{20}H_{21}N_3O_5S$ | Calc.; C 57.82, H 5.09, N 10.11<br>Found; C 57.57, H 5.04, N 10.05 |

EXAMPLE 27

N-[2-Methoxy-5-[(2,4-dioxothiazolidin-5-yl)methyl]phenyl]-2- 4-chlorophenyl)acetamide 5-[(3-Amlno-4-methoxyphenyl)methyl]thiazolidine-2,4-dione (250 mg, 0.991 mmol) and dehydrated methylene chloride (10 mL) were mixed, and, after 4-chlorophenylacetic acid (178 mg, 1.04 mmol) and 1-[3-(dimethylamino)propyl]-3-ethylcarbodiimide hydrochloride (228 mg, 1.19 mmol) were added under cooling with ice and stirring, the mixture was stirred for 20 minutes under cooling with ice. The reaction mixture was poured into water, which was extracted with methylene chloride. The extracted solution was washed with 5% hydrochloric acid, saturated aqueous solution of sodium hydrogencarbonate and brine in sequence, and then concentrated. The residue was recrystallized from mixed solvent of methanol with isopropyl ether to obtain 327 mg (82%) of the title compound as colorless powder.

Melting point 182.0–183.0° C.:
Mass analysis (EI$^+$) (m/z): 404 (M$^+$);
Elemental analysis (%) $C_{19}H_{17}ClN_2O_4S$: Calcd. (%) C, 56.36; H, 4.23; N, 6.92. Found (%) C, 56.27; H, 4.16; N, 6.88.

EXAMPLES 28 THROUGH 36

Similarly to Example 27, compounds in Table 2 were obtained.

TABLE 2

| Example | A | B | Melting point (° C.) | Charac. formula | Elemental analysis(%) |
|---|---|---|---|---|---|
| 28 | $CH_2CONH$ | 4-Me | 183.0–185.0 | $C_{20}H_2ON_2O_4S$ | Calc.; C 62.48, H 5.24, N 7.29<br>Found; C 62.32, H 5.16, N 7.21 |
| 29 | $CH_2CONH$ | 4-OMe | 124.0–125.0 | $C_{20}H_2ON_2O_5S$ *1/4$H_2O$ | Calc.; C 59.32, H 5.10, N 6.92<br>Found; C 59.43, H 4.90, N 6.89 |
| 30 | $CH_2CONH$ | 4-Ph(4-OMe) | 205.0–207.0 | $C_{26}H_{24}N_2O_5S$ *1/4$H_2O$ | Calc.; C 64.92, H 5.13, N 5.82<br>Found; C 65.15, H 5.06, N 5.76 |
| 31 | $CH_2CONH$ | 4-Ph(4-Me) | 189.0–191.0 | $C_{26}H_{24}N_2O_4S$ *1/4$H_2O$ | Calc.; C 67.15, H 5.31, N 6.02<br>Found; C 67.36, H 5.27, N 6.08 |
| 32 | $CH_2CONH$ | 4-Ph(4-Cl) | 193.0–195.0 | $C_{25}H_{21}ClN_2O_4S$ *1/4$H_2O$ | Calc.; C 61.85, H 4.46, N 5.77<br>Found; C 61.91, H 4.41, N 5.72 |
| 33 | $CH_2CONH$ | 4-OPh(4-Cl) | Amorphous | $C_{25}H_{21}ClN_2O_5S$ | Calc.; C 60.42, H 4.26, N 5.64<br>Found; C 60.12, H 4.28, N 5.47 |
| 34 | $CH_2CONH$ | 4-OCH2Ph(4-OMe) | 140.0–141.0 | $C_{27}H_{26}N_2O_6S$ | Calc.; C 64.02, H 5.17, N 5.53<br>Found; C 64.03, H 5.25, N 5.38 |
| 35 | $CH_2CONH$ | 4-OCH2Ph(4-Me) | 158.0–160.0 | $C_{27}H_{26}N_2O_5S$ | Calc.; C 66.10, H 5.34, N 5.71<br>Found; C 66.42, H 5.29, N 5.63 |
| 36 | $CH_2CONH$ | 4-OPh(4-Me) | 186.0–188.0 | $C_{26}H_{24}N_2O_5S$ | Calc.; C 65.53, H 5.08, N 5.88<br>Found; C 65.14, H 5.19, N 5.75 |

Biological Activity

TEST EXAMPLE 1

Test of Transactivation on Peroxtsome Proliferator-activated Receptor

To CHO cells cultured in a Ham's F-12 medium containing fatty acid free 10% fetal calf serum, receptor plasmid and its reporter plasmid (STRATAGENE Corp.) that express fused protein of DNA-binding domain being transcription factor of yeast with ligand-binding domain of human type PPARα and γ (Biochemistry, 1993, 32, 5598), and β-galactosidase plasmid (Promega Corp.) for internal standard were cotransfected with lipofectamine in the serum-free state. Thereafter, testing compound and control compound (Troglitazone and Pioglitazone for control drug of PPARγ, and (8S)-HETE for control drug of PPARα) were dissolved into DMSO and adjusted with Ham's F-12 medium containing fatty acid free 10% fetal calf serum, so that the final concentration of DMS0 became 0.01% to culture. After 24 hours, CAT activity and β-galactosidase activity were measured.

Results, are shown in Table 3. From these results, it was shown that the inventive compounds had potent transactivation action on human peroxisome proliferator-activated receptor α and γ.

TABLE 3

| | Transactivation action | |
|---|---|---|
| Example | PPARα $EC_{50}(\mu mol/L)$ | PPARγ $EC_{50}(\mu mol/L)$ |
| 6 | 0.60 | 3.30 |
| 11 | 0.55 | 0.43 |
| 15 | 0.86 | 1.10 |
| 22 | 0.80 | 0.40 |
| Troglitazone | — | 1.15 |
| Pioglitazone | — | 0.72 |
| (8S)-HETE | 1.30 | — |

Utilizability in the Industry

From the results as described above, the inventive substituted thiazolidine-2,4-dione derivatives are novel compounds with excellent human PPAR transactivation action.

From the fact that these inventive compounds have agonistic activity on human PPAR, it can be said that they are effective compounds as therapeutic drugs for diabetes and/or therapeutic drugs for hyperlipidemia aforementioned.

What is claimed is:

1. A substituted benzylthiazolidine-2,4-dione derivative represented by a general formula (1)

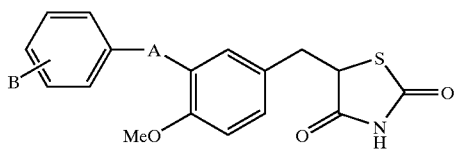

(1)

wherein the bond mode of A denotes —CH₂CONH—, —NHCONH—, —CH₂CH₂CO— or —NHCOCH₂—, and B denotes a lower alkyl group with carbon atoms of 1 to 4, lower alkoxy group with carbon atoms of 1 to 3, halogen atom, trifluoromethyl group, trifluoro-methoxy group, phenyl group which is unsubstituted or may have substituents, phenoxy group which is unsubstituted or may have substituents or benzyloxy group which is unsubstituted or may have substituents, their medicinally acceptable salts and their hydrates.

2. Substituted benzylthiazolidine-2,4-dione derivatives, their medicinally acceptable salts and their hydrates of claim 1, wherein the bond mode of A is —CH₂CONH—.

3. Substituted benzylthiazolidine-2,4-dione derivatives, their medicinally acceptable salts and their hydrates of claim 1, wherein the bond mode of A is —NHCONH—.

4. Substituted benzylthiazolidine-2,4-dione derivatives, their medicinally acceptable salts and their hydrates of claim 1, wherein the bond mode of A is —NHCOCH₂—.

5. Substituted benzylthiazolidine-2,4-dione derivatives, their medicinally acceptable salts and their hydrates of claim 1, wherein the bond mode of A is —CH₂CH₂CO—.

6. Compounds, their medicinally acceptable salts and their hydrates of claim 1, wherein one of the compounds is N-[2-methoxy-5-[(2,4-dioxothiazolidin-5-yl)methyl]phenyl]-2-[4-(trifluoromethyl)phenyl]acetamide.

7. Compounds, their medicinally acceptable salts and their hydrates of claim 1, wherein one of the compounds is 5-[[4-methoxy-3-[3-[4-(trifluoromethyl)phenyl]ureido]phenyl]-methyl]thiazolidine-2,4-dione.

8. Compounds, their medicinally acceptable salts and their hydrates of claim 1, wherein one of the compounds is N-[4-(trifluoromethyl)phenyl]-2-[5-[(2,4-dioxothiazolidin-5-yl)methyl]-2-methoxyphenyl]acetamide.

9. Compounds, their medicinally acceptable salts and their hydrates of claim 1, wherein one of the compounds is 5-[[3-[3-[4-(trifluoromethyl)phenyl]propanoyl]-4-methoxyphenyl]methyl]-thiazolidine-2,4-dione.

10. A medicinal composition, comprising at least one substituted benzylthiazolidine-2,4-dione derivative according to claim 1 and a suitable carrier.

11. A process for preparing a medicinal composition, comprising contacting at least one substituted benzylthiazolidine-2,4-dione derivative according to claim 1 with a suitable carrier.

* * * * *